United States Patent
Robinson

[11] Patent Number: 6,030,218
[45] Date of Patent: Feb. 29, 2000

[54] OSSEO-INTEGRATED SUB-PERIOSTEAL IMPLANT

[76] Inventor: Dane Q. Robinson, 8330 E. Captain Dreyfus, Scottsdale, Ariz. 85260

[21] Appl. No.: 09/290,098

[22] Filed: Apr. 12, 1999

[51] Int. Cl.[7] ................. A61C 8/00; A61F 2/28
[52] U.S. Cl. .............................. 433/173; 623/16
[58] Field of Search .................... 433/173, 174, 433/175, 176, 215; 623/16

[56] References Cited

U.S. PATENT DOCUMENTS

| | | | |
|---|---|---|---|
| 3,683,422 | 8/1972 | Stemmer et al. | 623/16 |
| 4,359,318 | 11/1982 | Gittleman | 433/173 |
| 4,636,215 | 1/1987 | Schwartz | 623/16 |
| 4,787,906 | 11/1988 | Haris | 623/16 |
| 5,221,204 | 6/1993 | Kruger et al. | 433/173 |
| 5,306,149 | 4/1994 | Schmid et al. | 433/173 |
| 5,372,503 | 12/1994 | Elia | 433/173 |
| 5,460,526 | 10/1995 | Bosker | 433/173 |
| 5,489,305 | 2/1996 | Morgan | 623/16 |
| 5,580,247 | 12/1996 | Gittleman | 433/173 |
| 5,839,899 | 11/1998 | Robinson | 433/215 |

*Primary Examiner*—Ralph A. Lewis
*Attorney, Agent, or Firm*—Michael A. Lechter; Squire, Sanders & Dempsey

[57] ABSTRACT

A sub-periosteally implantable prosthesis support structure for a fixed or detachable dental prosthesis includes a framework fitted to and generally conforming to the inner and outer contours of the bony ridge structures of a person. The framework is configured to provide a space extending generally normal to the bony ridge structure to an apex to provide space for subsequent bone growth. A plurality of denture support posts are distributed about the framework and depend outwardly from the apex in substantial alignment with the bony ridge structure. During the fabrication of the prosthesis support structure, a bio-compatible fine mesh screen is fixed to and spans, tent-like, the framework to substantially overlay the bone structure and the space provided for subsequent bone growth. After the support structure has been implanted, the growth of bone into the space and around the support structure is promoted to osseo-integrate the support structure with the person's bony ridge, thus providing a secure foundation for a denture or fixed dental prosthesis configured for detachable or fixed coupling with the denture support posts. The support structure may be made, partly or wholly, from either non-resorbable material, such as titanium stock and mesh, or from a resorbable material such as Vicryl™.

15 Claims, 6 Drawing Sheets

OSSEO-INTEGRATED SUB-PERIOSTEAL IMPLANT

FIELD OF THE INVENTION

This invention relates to the art of dentistry and, more particularly, to devices which relate to the surgical placement of permanent dental support structures in the maxillary (upper) and mandibular (lower) jaw bones, which support structures are adapted to connectively receive complementarily-configured dental prostheses.

BACKGROUND OF THE INVENTION

For many years, persons who have lost their natural teeth have used full dentures as functional and aesthetic replacements. The most common configuration has been those dentures which have been individually fitted to a person's upper and lower gum structures as they exist at the time of fitting. When this procedure is carried out by a skillful dentist, with the assistance of a competent dental laboratory, the results can be satisfactory, at least for a time. However, such conventional dentures, which are held in place frictionally (and, to some extent, by suction and sometimes by the supplementary employment of special adhesive powder or paste), often are subject to failure to hold their intended positions. This failure mode, which can increase in frequency as a person's gum structures alter over a period of time, subject the wearer to embarrassment and eventually render the dentures significantly less functional and subject to replacement.

Over the years, dental researchers and innovators have striven to develop other approaches to the replacement of lost natural teeth. For example, individual tooth implants have been successfully carried out, and this procedure is now relatively common. However, this is an uncomfortable, expensive and time consuming process which may not be suitable for many dental patients due to a lack of available bone.

Another process which has been developed employs a series of spaced apart support posts which are individually emplaced into a person's upper and/or lower bony ridge. The support posts (typically eight for each of the maxillary and mandibular positions) depend more or less downwardly from the maxillary bony ridge and more or less upwardly from the mandibular bony ridge. The outward end of each support post typically terminates in a small orb or ball shape. A special denture is prepared which includes a series of openings on its underside. The series of openings are complementarily positioned and dimensioned to receive and frictionally securely engage the orb-shaped end of each support post. The resulting detachable denture system can be very satisfactory.

However, a significant problem with denture systems which employ support posts to engage and hold specially-configured dentures in place is the underlying security of the support posts. There may be, at the time of emplacement or later, insecurity at the bases of the support posts fixed in a patient's bony ridge, notwithstanding the most careful dental work. Similarly, some patients who would otherwise benefit greatly from the emplacement of such a denture system may have insufficient bony ridge structure to receive and securely hold the support post series.

There has been developed an advanced dental technique which may permit those patients who have insufficient bone structure to reliably receive and hold support posts to still enjoy the benefit of detachable dentures or a fixed coupled to such support posts. This technique, which is presently outside the mainstream of dentistry, employs a maxillary and/or mandibular framework emplaced sub-periosteal, but resting on the existing bone structure with the denture support posts depending from a bar carried at the apex of each framework. Implants of this type have had good success, particularly when made in the mandibular position, but are subject to important objections, particularly as used in the maxillary position because of, inter alia, the thinness of the maxillary bone.

One reason for the limited acceptance of sub-periosteal implants is the broad perception that the implant has a high degree of framework strut exposure which is a result of a lack of bone attachment to and around the struts as well as unsatisfactory soft tissue healing. As a result, the implants, particularly in the maxillary position, are subject to infection. It is to an improved dental implant system of this type which alleviates these and other problems to which the present invention is directed.

OBJECTS OF THE INVENTION

It is therefore a broad object of this invention to provide an improved dental implant system of the type in which a specially-configured dental prosthesis is detachably coupled with support posts which depend from a sub-periosteal framework implant.

It is a more particular object of this invention to provide such an improved dental implant system in which the framework is much more securely implanted and therefore provides corresponding improved strength, health and longevity of the system.

It is a still more particular object of this invention to provide such an improved dental implant system in which, during the process of implanting the series of support posts, growth of a patient's bony ridge under and around a framework structure incorporating the support posts is promoted in order to obtain an osseo-integrated support structure. Accordingly, the long term strength of the dental prosthesis support structure is greatly enhanced. In addition, the successful use of such an improved dental implant system can be achieved in those patients who, with corresponding prior art systems, were not suitable candidates because of insufficient bony ridge structure at the time the implanting process is instituted.

SUMMARY OF THE INVENTION

Briefly, these and other objects of the invention are achieved by a sub-periosteally implantable dental prosthesis support structure for a fixed or detachable dental prosthesis which includes a framework fitted to and generally conforming to the inner and outer contours of the maxillary and/or mandibular bony ridge structures of a person. The framework is configured in cross section to provide a space extending generally normal to the bony ridge structure to an apex to provide space beneath the apex for subsequent bone growth. A plurality of dental prosthesis support posts are distributed about and affixed to the framework and depend outwardly from the apex in substantial alignment with the bony ridge structure of the person when said support structure has been sub-periosteally implanted. During the fabrication of the prosthesis support structure, a bio-compatible fine mesh screen is fixed to and spans, tent-like, the framework to substantially overlay the implant structure and the space provided for subsequent bone growth. After the support structure has been sub-periosteally implanted, the growth of bone into the space and around the support structure is promoted to osseo-integrate the support structure with the person's bony ridge, thus providing a secure foundation for a dental prosthesis configured for coupling with the sub-periosteal dental implant support posts. Preferably, the support structure adapted for use in the maxillary position incorporates a plurality of integral pads positioned to abut the person's bony ridge such that subsequent bone growth securely embeds the pads to provide additional security to the support structure. The weave overlay may be made from either non-resorbable material, such as titanium cloth, or from a resorbable material such as Vicryltm.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

DESCRIPTION OF THE PREFERRED EMBODIMENT(S)

Figure 1:
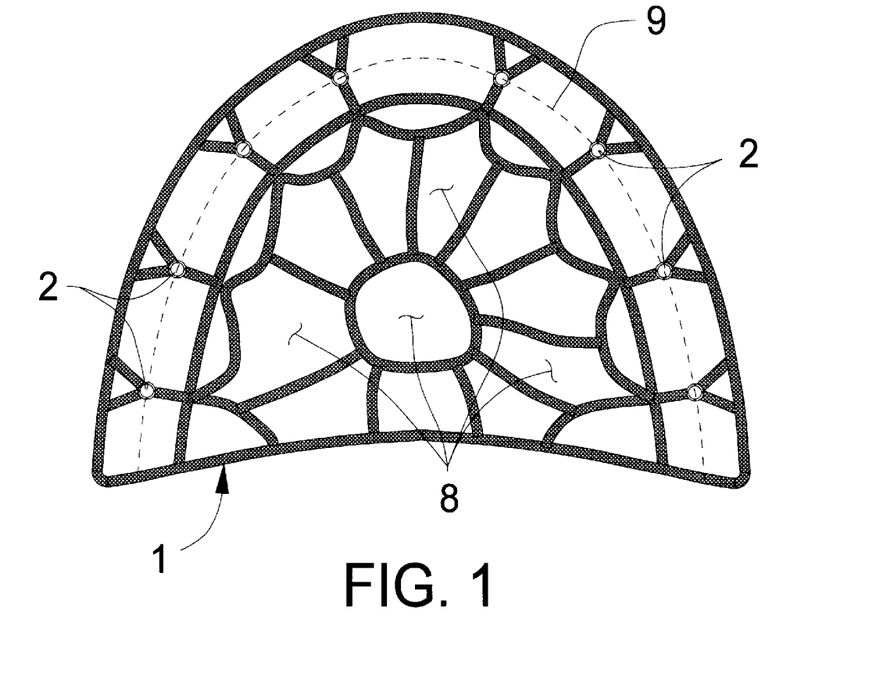
FIG. 1 is a plan view of the framework of a prosthesis support structure suitable for use in the maxillary position and which serves to both provide support posts for a detachable denture and to promote growth of the bony ridge.

Attention is first directed to FIG. 1 which illustrates a first version of an important component of the inventive apparatus. More particularly, there is shown in FIG. 1, a plan view of a framework 1 of a prosthesis support structure suitable for use in the maxillary position and which serves to both provide a series of support posts 2 for a receiving a detachable denture and to promote growth of the maxillary bony ridge of a patient to which the prosthesis support structure has been fitted. Preferably, each of the support posts 2 is supported at the junction of framework members at the apex 9 of the framework. As will become more evident below, the under side of framework 1 fits intimately against the existing bone. The framework 1 extends into a palate abutment region 8 to provide additional rigidity and security when in place. The individual framework members may be joined in any suitable manner such as by the use of an adhesive, by welding (particularly spot welding) or sintering, or, if appropriate to the material selected, the framework 1 may preferably be cast as an integral unit.

Figure 2:
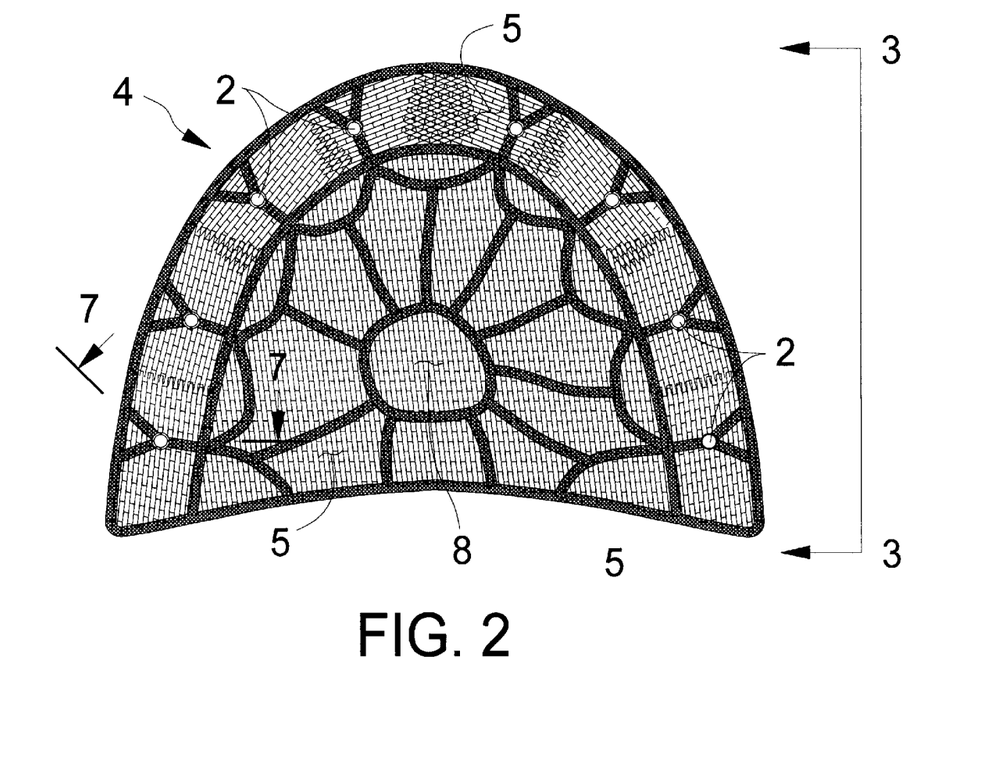
FIG. 2 is a view similar to FIG. 1 further illustrating a fine mesh, for example of titanium, overlaying the framework.
Figure 3:
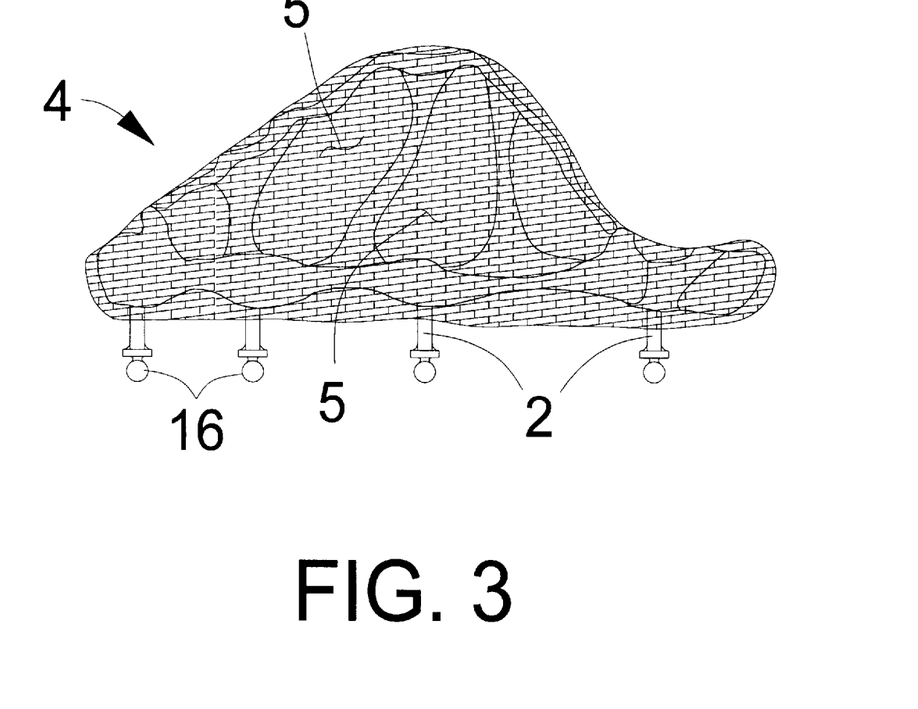
FIG. 3 is a side view of the prosthesis support structure for use in the maxillary position taken as indicated at 3—3 of FIG. 2.

Referring also to FIGS. 2 and 3, the framework 1 is shown covered with a mesh screen 5, which may be fabricated, for example, from titanium, to effect a complete prosthesis support structure 4 for use in the maxillary position as will be described more fully below. In practice, the screen 5 may be fabricated from any bio-compatible material suitable as to strength and appropriate for permanent retention in the mouth of an individual. Further, for some applications, the screen 5 may alternatively be fabricated from a resorbabale material such as Vicryl™. The purpose of the screen is to create a tenting of the gum tissue above the bone in order that bone will grow between and to the frame and into the weave. In addition, it serves to provide a rigid, biocompatible structure for the gum tissue to become attached in its new, tented position.

Figure 4:
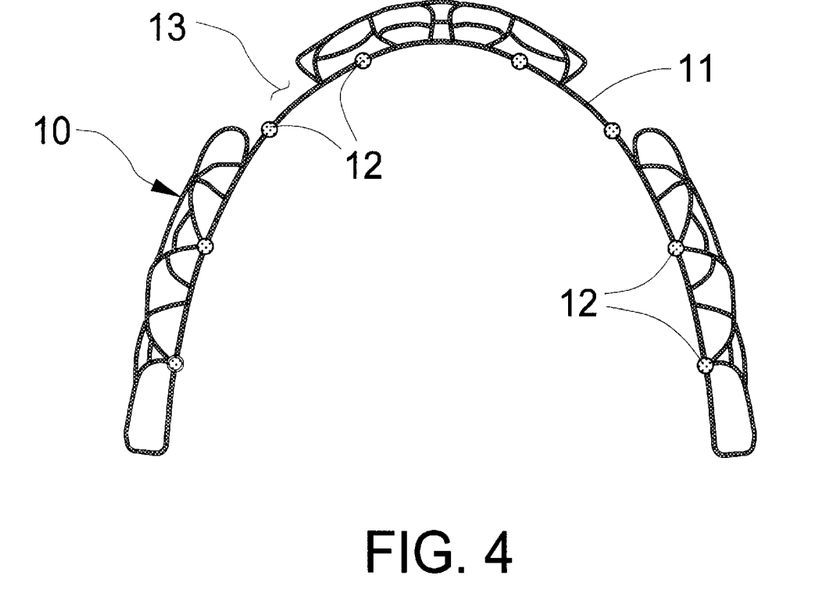
FIG. 4 is a plan view of the framework of a prosthesis support structure suitable for use in the mandibular position and which serves to both provide support posts for a detachable denture and to promote growth of the bony ridge.

Similarly, FIG. 4 illustrates, in plan view, a second version of a framework 10 for a prosthesis support structure suitable for use in the mandibular position and which serves to both provide a series of support posts 12 for a receiving a fixed dental prosthesis and to promote growth of the bony ridge of a patient to which the prosthesis support structure has been fitted. Nonetheless, it may be appropriate, for a given individual in certain situations, to also include abutment pads with the framework 10 used in the mandibular or maxillary position, and the conditions which might call for such inclusion will be discussed below. Further, the framework 10 is provided with a bar member 11 extending about its apex, and the respective bases of the support posts 12 are affixed to the bar member. However, of course, there is no need for providing a palate region (corresponding to the palate region 8 of the framework 1) of the framework 10 which would, in any event, interfere with the tongue of a patient.

Figure 5:
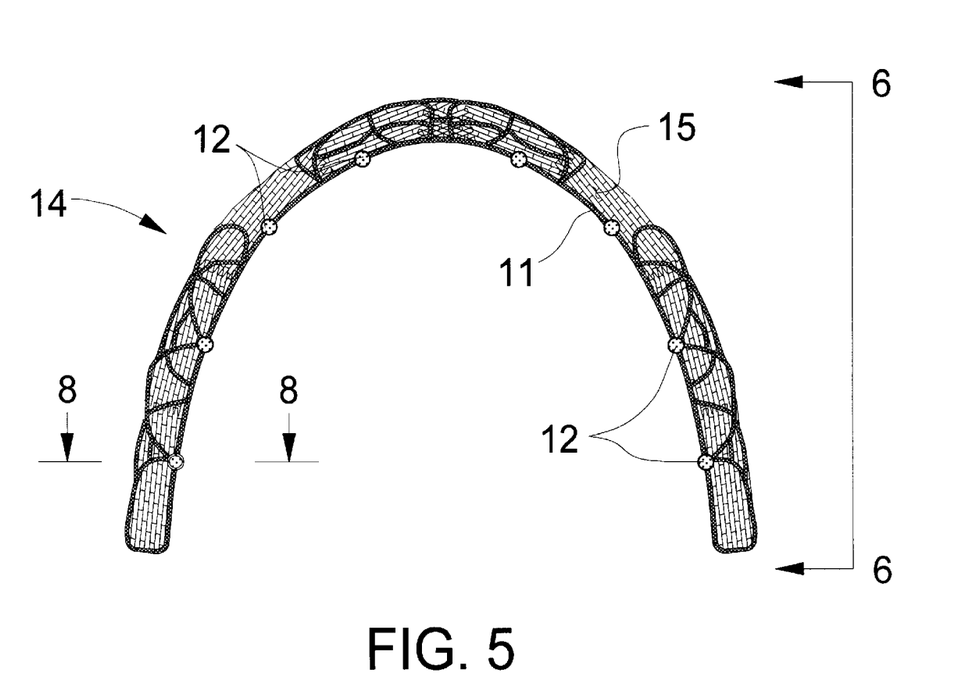
FIG. 5 is a view similar to FIG. 3 further illustrating a fine mesh, for example of titanium, overlaying the framework.
Figure 6:
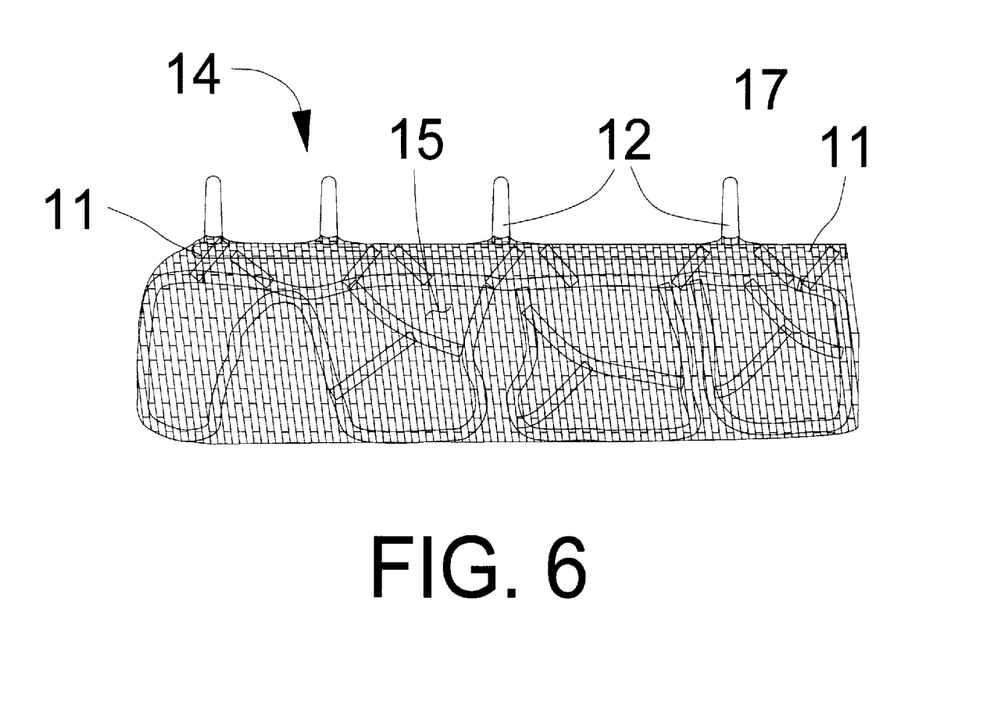
FIG. 6 is a side view, rotated 180° to indicate a functional relationship with FIG. 5, of the prosthesis support structure for use in the mandibular position taken as indicated at 6—6 of FIG. 5.

Referring also to FIGS. 5 and 6, the framework 10 is shown covered with a mesh screen 15 to effect a complete prosthesis support structure 14 for use in the mandibular position. The screen 15, like the screen 5, may be fabricated from any material suitable as to strength and appropriate for permanent retention in the mouth of an individual, and the presently preferred material is titanium, the alternative materials having been discussed above. The frameworks 1, 10 are, themselves made of a suitable material, such as titanium stock, for lightness and strength as well as appropriateness for permanent emplacement in a patient's mouth. Similarly, the mesh 5, 15 may be attached to the framework 1, 10 by any suitable means such as with an adhesive or by welding, spot welding being particularly suitable when the presently preferred material, titanium, is used, or by sintering or even by the use of suitably placed ligatures.

The mesh 5, 15 should be sufficiently open as to permit nutrients to readily pass to the underlying tissue, but strong enough to establish a relatively rigid structure in use. It has been found that, when titanium mesh is employed, on the order of 0.003 inch wire in about a 50×50 wires per inch weave is a very suitable mesh for the intended purpose. The titanium stock from which the frameworks are fabricated can be on the order of 0.050 –0.200 inch thickness; however, the presently preferred method of fabricating the frame is as a one-piece casting.

In the case of the mandibular framework 10 and support structure 14 shown in shown in FIGS. 4 and 5, it will be observed that bilateral spaces 13 along the length of the framework are provided, spanned only by the bar 11 and screen 15, in order to prevent any unintended interference with the mental nerve.

The side views of FIGS. 3 and 6 respectively particularly well illustrate the downward dependency of the maxillary denture-receiving support posts 2 from the prosthesis support 4 and the upward dependency of the mandibular fixed cementable prosthesis support posts 12 from the prosthesis support 14. (It will be understood that fixed cementable prosthesis support posts 12 can also be employed with the prosthesis support 4 for a suitable patient environment.) Accordingly, FIGS. 3 and 6 can be viewed together to better appreciate the structures which would be appropriate to a patient receiving both maxillary and mandibular implants.

The support posts 2, 12 terminate at their unsupported ends in respective orb or ball structures 16 or abutment posts 17 which, as already known in the art, are dimensioned and configured to receive and frictionally engage apertures in a detachable dental prosthesis or to receive a cemented prosthesis to thereby securely fix such prostheses in place.

Those skilled in the dental arts will understand that the rather regular and symmetrical prosthesis supports 4, 14 shown in FIGS. 1–6 are idealized and that those prosthesis supports prepared for an individual patient may, in fact, be considerably irregular and asymmetrical. It will be understood by those skilled in the art that the complete prosthesis supports 4, 14 are individually fabricated by a dental technician over a casting made from impressions of a given patient's maxillary and/or mandibular gum/bony ridge regions. Thus, each prosthesis support 4 and/or 14 will be a close, tent-like fit over the maxillary and/or mandibular bone structures and under the gum tissue of the given patient at the time of fitting.

Figure 7:
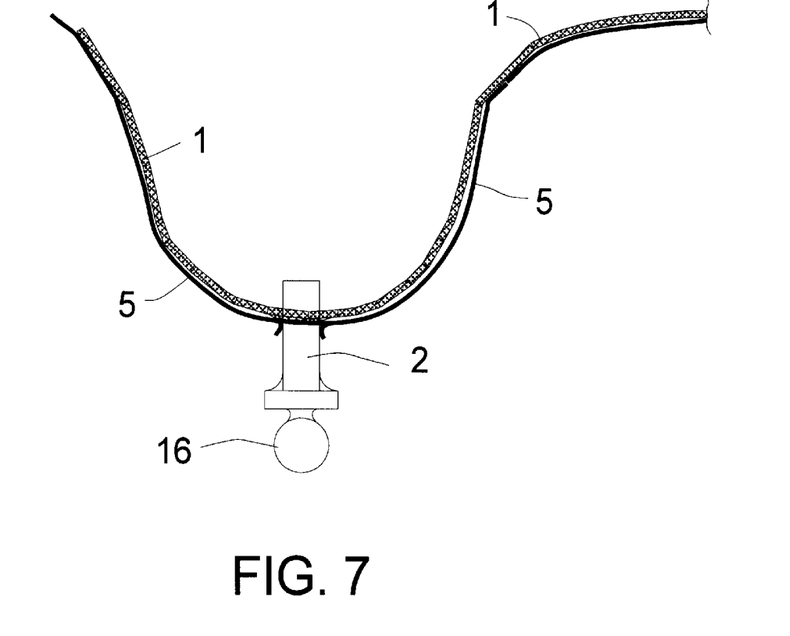
FIG. 7 is a cross sectional view taken along the angled lines 7—7 of FIG.2.
Figure 8:
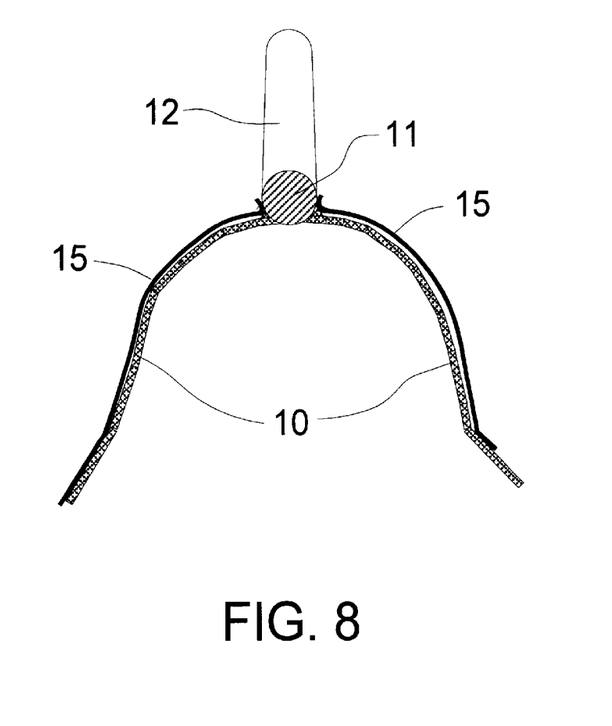
FIG. 8 is a cross sectional view taken along the lines 8—8 of FIG. 5.

Consider now FIG. 7 which is a cross sectional view of the prosthesis support 4 taken along the angled lines 7–7 of FIG. 2. The lines are angled in order to show the tent-like configuration of the cross section. As previously discussed, the screen 5 overlays and is fixed to the framework 1 with the support posts 2 depending downwardly from the framework. Similarly, FIG. 8 is a cross sectional view taken along the lines 8–8 of FIG. 5 illustrating the similar, but not identical, configuration for a prosthesis support 14 which is appropriate for use in the mandibular position of a given patient. The screen 15 overlays and is fixed to the framework 10 with the support posts 12 fixed to and depending upwardly from the bar 11.

Figure 9:
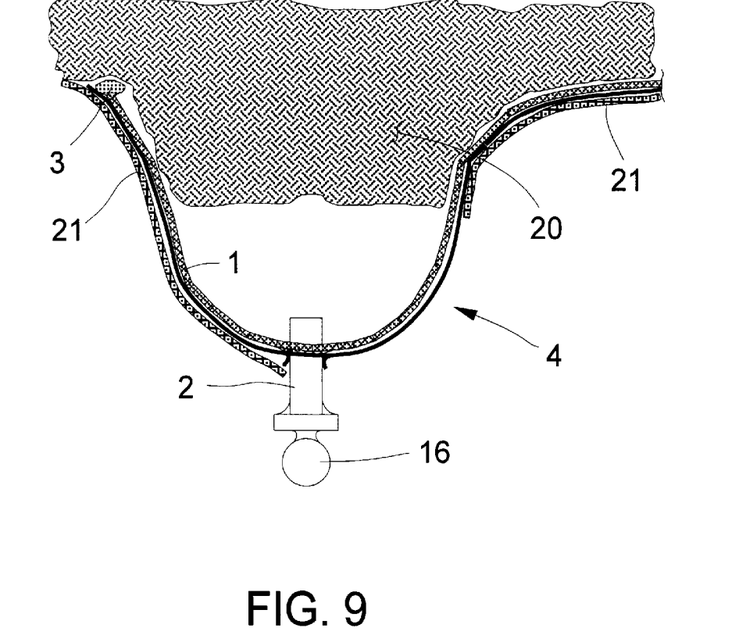
FIG. 9 is a view similar to FIG. 7 illustrating the relationship between the prosthesis support structure and the maxillary bony ridge structure of a patient when the prosthesis support structure has been fitted to the patient.
Figure 10:
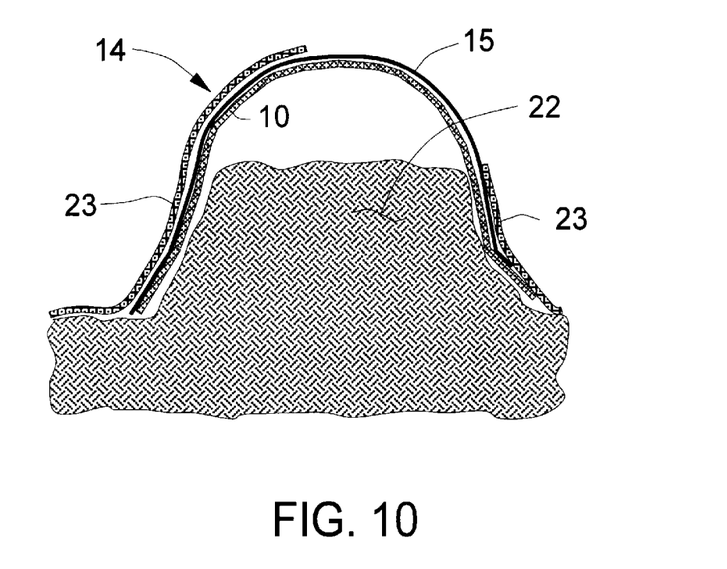
FIG. 10 is a view similar to FIG. 6 illustrating the relationship between the prosthesis support structure and the mandibular bony ridge structure of a patient when the prosthesis support structure has been fitted to the patient.

Attention is now directed to FIGS. 9 and 10 which illustrate, respectively, cross sections of the prosthesis supports 4, 14 after emplacement in the maxillary and mandibular positions in a patients mouth. Referring specifically to FIG. 9, the prosthesis support 4 has been surgically placed against and overlaying the patients maxillary bony ridge 20 and beneath the adjacent soft tissue 21. Further, it will be noticed that the gum tissue 21 is separated from the bony ridge 20 by at least the thickness of the struts making up the framework 1, a condition which has been found conducive to the encouragement of subsequent bone growth. Similarly, as shown in FIG. 10, the mandibular prosthesis support 14 is shown as it has been surgically implanted over the mandibular bony ridge 22 and beneath the surrounding soft tissue 23. This embodiment does not have prosthetic support posts and is meant to recreate a new alveolar bony ridge for future implantation.

Figure 11:
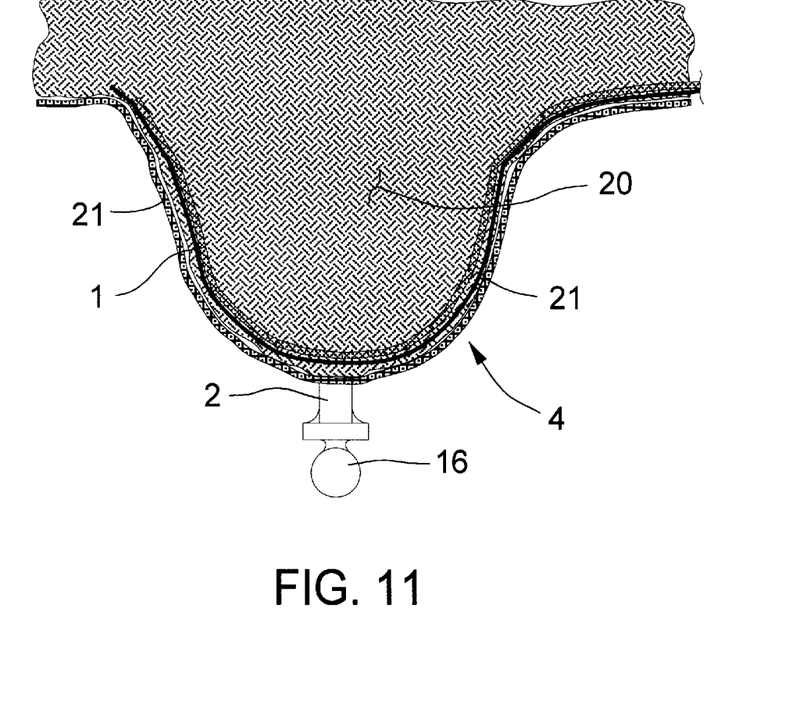
FIG. 11 is a view similar to FIG. 9 illustrating the relationship between a prosthesis support structure and the maxillary bony ridge structure of a patient after the prosthesis support structure has been worn for some time by the patient and particularly showing the intervening growth of the maxillary bony ridge structure.
Figure 12:
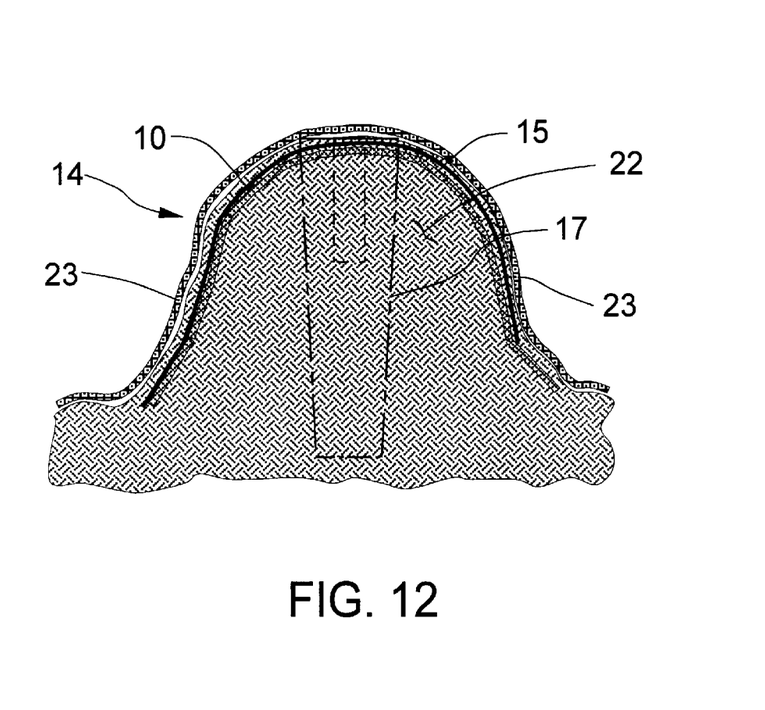
FIG. 12 is a view similar to FIG. 11 illustrating the relationship between a prosthesis support structure and the mandibular bony ridge structure of a patient after the prosthesis support structure has been worn for some time by the patient and particularly showing the intervening growth of the mandibular bony ridge structure.

Attention is now directed to FIGS. 11 and 12 which shows the same environment as FIGS. 9 and 10, respectively, but after the prosthesis supports 4, 14 have been in place for a period which may range, for an individual patient, from several weeks to several months. More particularly, with reference to FIG. 11, it will be seen that the bony ridge 20 of the maxillary region has grown to substantially completely encompass the prosthesis support 4. The overlying tissue 21 is substantially continuously overgrown in the region such that only the outboard ends of the support posts 2 (carrying the ball ends 16) project into the patient's oral cavity.

Similarly, as shown in FIG. 12, the mandibular bony ridge 22 has grown to more or less completely encompass the support prosthesis 14, and the surrounding soft tissue 23 has become a continuous layer over the support prosthesis 14. Once a bony ridge has formed, a conventional implant can be placed into the newly formed bony ridge.

It has been previously noted that the prosthesis support structure 14 need not necessarily be made, in part or in whole, of a non-resorbable material such as titanium. In fact, the use of a resorbable material for fabricating a portion or all the prosthesis support structure(s) is contemplated as previously described. Thus, it will be seen from an examination of FIG. 12 that if a resorbable material, such as Vicryl™, has been used to fabricate all or part of the support prosthesis 14. A bony ridge will be created after the resorbable material has been naturally absorbed and has, in effect, disappeared. A conventional implant 17 may then be placed in the augmented bony ridge.

Those skilled in the art will understand that the various embodiments of the invention set forth above may be incorporated into either a full arch as illustrated or a partial arch as may be appropriate for a prosthesis prepared for a given patient.

Thus, while the principles of the invention have now been made clear in an illustrative embodiment, there will be immediately obvious to those skilled in the art many modifications of structure, arrangements, proportions, the elements, materials, and components, used in the practice of the invention which are particularly adapted for specific environments and operating requirements without departing from those principles.

What is claimed is:

1. A sub-periosteally implantable support structure for supporting a detachable or fixed dental prosthesis comprising:

A) a framework in at least a partial arch fitted to and generally conforming to the inner and outer contours of one of the maxillary and mandibular bony ridge structures of a person, said framework being configured in cross section to provide a space extending generally normal to the bony ridge structure to provide space beneath the outer surface of said framework for subsequent bone growth;

B) a plurality of denture support posts, said denture support posts being distributed about and affixed to said framework and depending outwardly from said apex in substantial alignment with the bony ridge structure of the person when said support structure has been sub-periostally implanted; and C) a bio-compatible fine mesh screen fixed to and spanning said framework to substantially overlay the framework fitted to one of the maxillary and mandibular bony ridges of the person to which said framework has been fitted, said fine mesh screen also overlaying said space provided for subsequent bone growth, thereby allowing for gum and soft tissue attachment to said fine mesh screen;

whereby, after said support structure has been sub-periostally implanted, the growth of bone into said space and around said support structure is promoted to osseo-integrate said support structure with the person's bony ridge, thus providing a secure foundation for a dental prosthesis configured for coupling with said dental prosthesis support posts.

2. The dental prosthesis support structure of claim 1 in which said framework constitutes a full arch.

3. The denture support structure of claim 2 in which said framework is fabricated from titanium struts.

4. The dental prosthesis support structure of claim 1 in which said framework constitutes a partial arch.

5. The denture support structure of claim 4 in which said framework is fabricated from titanium struts.

6. The dental prosthesis support structure of claim 1 in which said screen is fabricated from titanium.

7. A sub-periosteally implantable support structure for creating space to grow bone comprising:

A) a framework in at least a partial arch fitted to and generally conforming to the inner and outer contours of one of the maxillary and mandibular bony ridge structures of a person, said framework being configured in cross section to provide a space extending generally normal to the bony ridge structure to provide space beneath the outer surface of said framework for subsequent bone growth;

B) a bio-compatible fine mesh screen fixed to and spanning said framework to substantially overlay the framework fitted to one of the maxillary and mandibular bony ridges of a person to which said framework has been fitted, said fine mesh screen also overlaying said space provided for subsequent bone growth, thereby allowing for gum and soft tissue attachment to said fine mesh screen;

whereby, after said support structure has been sub-periostally implanted, the growth of bone into said space and around said support structure is promoted.

8. The support structure of claim 7 in which said framework constitutes a full arch.

9. The structure of claim 8 in which said framework is fabricated from titanium struts.

10. The support structure of claim 8 in which said screen is fabricated from a resorbable material.

11. The support structure of claim 7 in which said framework constitutes a partial arch.

12. The support structure of claim 11 in which said screen is fabricated from titanium.

13. The support structure of claim 11 in which said screen is fabricated from a resorbable material.

14. The support structure of claim 7 in which said screen is fabricated from titanium.

15. The support structure of claim 7 in which said screen is fabricated from a resorbable material.

* * * * *